under a patent application filed by the United States. The following is a description of the invention.

United States Patent [19]
Keefer et al.

[11] Patent Number: 5,250,550
[45] Date of Patent: Oct. 5, 1993

[54] COMPLEXES OF NITRIC OXIDE WITH POLYAMINES

[75] Inventors: Larry K. Keefer, Bethesda; Joseph A. Hrabie, Frederick, both of Md.

[73] Assignee: The Government of the United States of America as represented by the Secretary of the Department of Health and Human Services, Washington, D.C.

[21] Appl. No.: 906,479

[22] Filed: Jun. 30, 1992

Related U.S. Application Data

[63] Continuation of Ser. No. 585,793, Sep. 20, 1990, Pat. No. 5,155,137.

[51] Int. Cl.[5] .............................................. A01N 43/40
[52] U.S. Cl. ................................... 514/357; 544/382; 546/205; 546/206; 546/223; 546/244; 546/264; 546/329; 546/332; 514/319; 514/329; 514/332; 514/611
[58] Field of Search ............... 546/244, 246, 247, 264, 546/332, 205, 206, 223, 329; 514/255, 315, 351, 332, 319, 329, 357

[56] References Cited

PUBLICATIONS

Marmo et al. *Biomed. Biochem. Acta.* 43:509–15 (1984).
Palmer et al. *Nature* 327:524–6 (1987).
Robert F. Furchgott, Ann. Rev. Pharm. Toxicol., 1984, 24:175–97.
H. Kruszyna et al, Toxicology and Applied Pharmacol., 1987, 91:429–438.
Louis J. Ignarro, The FASEB Journal, vol. 3, Jan. 1989; pp. 31–36.
Louis J. Ignarro et al, The Journal of Pharmacology and Experimental Therapeutics, vol. 218, No. 3, 1981; pp. 739–749.
Raymond Longhi et al, Inorg. Chemistry, 1(3), 768–770 (1962).
Daniel O. Alonso Garrido et al, Am. Chem. Soc., 1984, vol. 49, pp. 2021–2023.
Raymond J. Bergeron, Acc. Chem. Res. 1986, vol. 19, pp. 105–113.
Raymond J. Bergeron et al, J. Org. Chem. 1984, vol. 49, pp. 2997–3001.
Raymond J. Bergeron et al, J. Org. Chem., 1988, vol. 53, pp. 3108–3111.
Tetrahedron Letters, vol. 29, No. 11, pp. 1279–1282, 1988. Carboni et al.
Henry E. Reich et al J. Amer. Chem. Soc., vol. 77, 5434–5436 (1955).
George Magnus et al, J. Amer. Chem. Soc., vol. 78, pp. 4127–4130 (1956).
R. S. Drago et al, J. Am. Chem. Soc., vol. 83, pp. 1819–1822 (1961).

*Primary Examiner*—Glennon H. Hollrah
*Assistant Examiner*—Brian M. Burn
*Attorney, Agent, or Firm*—Birch, Stewart, Kolasch & Birch

[57] ABSTRACT

There are disclosed novel complexes of nitric oxide and polyamines which are useful in treating cardiovascular disorders, including hypertension. The disclosed compounds release nitric oxide (endothelium-derived relaxing factor) under physiological conditions in a sustained and controllable fashion, and possess long mechanisms of action.

13 Claims, No Drawings

COMPLEXES OF NITRIC OXIDE WITH POLYAMINES

This application is a continuation of copending application Ser. No. 07/585,793, filed on Sep. 20, 1990, now U.S. Pat. No. 5,155,137, the entire contents of which are hereby incorporated by reference.

FIELD OF THE INVENTION

The present invention is concerned with providing stable complexes of nitric oxide with certain polyamines, which complexes are useful in treating cardiovascular disorders, including hypertension.

Related compounds with the same utility are described in Ser. No. 07/316,958, filed on Feb. 28, 1989, now U.S. Pat. No. 4,954,526; Ser. No. 07/409,552, filed on Sep. 15, 1989, now U.S. Pat. No. 5,039,705, and Ser. No. 07/423,279, filed on Oct. 18, 1989 now U.S. Pat. No. 5,212,204; all of which are incorporated by reference.

BACKGROUND OF THE INVENTION

Endothelium-derived relaxing factor (EDRF) is a labile humoral agent which is part of a cascade of interacting agents involved in the relaxation o vascular smooth muscle. EDRF is thus important in the control of vascular resistance to blood flow and in the control of blood pressure. Some vasodilators act by causing EDRF to be released from endothelial cells. (See Furchgott, Ann. Rev. Pharmacol. Toxicol. 24, 175-197, 1984). Recently, Palmer et al have shown that EDRF is identical to the simple molecule, nitric oxide, NO. (Nature 317, 524-526, 1987). It has been hypothesized for years that many nitrovasodilators that mimic the effect of EDRF, like glyceryl trinitrate, amyl nitrite, $NaNO_2$, and sodium nitroprusside (SNP), do so by virtue of their conversion to a common moiety, namely NO, which is also a vasodilator. (See Kruszyna et al, Tox. & Appl. Pharmacol. 91, 429-438, 1987; Ignarro, FASEB J. 3, 31-36, 1989; Ignarro et al, J. Pharmacol. Exper. Therapeutics 218 (3), 739-749, 1981).

Keefer et al, in U.S. Pat. No. 4,954,526, disclose a method of treating cardiovascular disorders in mammals by administering stabilized nitric oxide primary amine complexes to mammals in need thereof. U.S. Pat. No. 4,954,526 is expressly incorporated by reference.

Spermine is a polyamine (a molecule containing several amino functions) that by itself has been reported to show some hypotensive activity (Marmo, Berrino, Cazzola, Filippelli, Cafaggi, Persico, Spadaro and Nistico, Biomed. Biochim. Acta, 1984, 43, 509-515).

Longhi et al, in Inorganic Chemistry, 1(3), 768-770 (1962), reported that their reaction of N,N'-dimethylethylenediamine with nitric oxide utilizing high pressure techniques produced the compound Me-N($N_2O_2^-$)C-$H_2$—$CH_2$—N($N_2O_2^-$)Me  Me—$NH_2^+$—$CH_2$—$CH_2$—$NH_2^+$Me. Based upon preliminary studies made by the present inventors, Longhi et al may have instead produced a compound of the structure $CH_3NH_2^+CH_2CH_2N(N_2O_2^-)CH_3$. No uses are reported by Longhi et al for the compound prepared.

SUMMARY OF THE INVENTION

There is growing evidence that nitric oxide is released from the endothelial cells that line all blood vessels in the body during a key step in the normal relaxation of the underlying vascular smooth muscle and hence plays a crucial role in controlling blood pressure. Thus, one object of the present invention is to develop compounds which can, in a controlled manner, release nitric oxide in vivo.

Another object of the present invention is to provide complexes of nitric oxide and polyamines, which complexes are unusually stable, long acting, and potent cardiovascular agents when compared with prior known nitric oxide-amine complexes.

Still another object of the present invention is to provide methods of treating cardiovascular disorders using the stable and potent nitric oxide polyamine complexes herein disclosed, and to provide pharmaceutical compositions which contain such complexes.

Accordingly, the present invention provides the following Formulas I, II and III:nitric oxide-polyamine complexes and pharmaceutically acceptable salts thereof as useful cardiovascular agents.

Formula I:

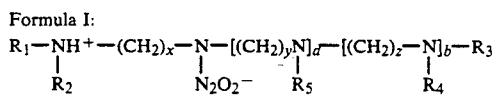

FORMULA II:

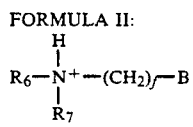

FORMULA III:

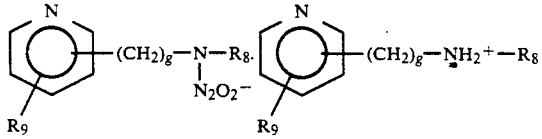

In the above Formulas I, II and III, b and d are independently zero or one; x, y and z are independently two to twelve; $R_1$ to $R_8$ are independently hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl; $R_9$ is hydrogen or a $C_1$-$C_{12}$ straight or branched chain alkyl; B is

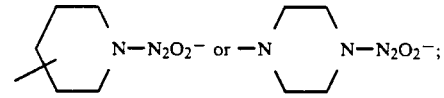

f is zero to twelve, with the proviso that when B is the substituted piperazine moiety

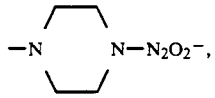

then f is two to twelve; and g is two to six. The group $—N_2O_2^-$ has the structure

The compounds of Formulas I, II and III encompassed hereby, are thought novel with the exception of the Formula I compound, wherein $R_1$ and $R_3$ are methyl, $R_2$ is hydrogen, x is 2, and b and d are zero. I5

Preferred among the above compounds of Formulas I and II, are those compounds wherein $R_1$ to $R_7$ are independently hydrogen, $C_{3-8}$ cycloalkyl, $C_{1-12}$ straight or branched chain alkyl, benzyl or acetyl. More preferred among the above compounds are those wherein $R_1$ to $R_7$ are independently hydrogen, methyl, ethyl, benzyl or acetyl, and x y and z are two to four.

Preferred compounds of Formula III include those compounds wherein $R_8$ is $C_{5-6}$ cycloalkyl, $C_{1-4}$ straight or branched chain alkyl, benzyl or acetyl. More preferred are compounds wherein $R_8$ is methyl, ethyl, benzyl or acetyl, and most preferred are compounds wherein $R_8$ is methyl or acetyl.

In addition to methods of treating cardiovascular disorders utilizing the above Formulas I, II and III compounds, there are also encompassed hereby pharmaceutical compositions which comprise a compound of Formulas I, II or III, or a pharmaceutically acceptable salt thereof, and a pharmaceutically acceptable carrier therefor.

All compounds encompassed by Formulas I-III are useful in the pharmaceutical methods and compositions disclosed herein.

DETAILED DESCRIPTION OF THE INVENTION

The following detailed description is provided in order to aid those skilled in the art in practicing the present invention. Even so, the following discussions should not be thought to unduly limit the present invention. In this regard, it is especially noted that those of ordinary skill in the art, upon review of the present disclosure, may realize that certain variations may be made in the synthesis methods, methods of administration, etc., disclosed herein, while still achieving the objects of the present invention. As such, these variations are deemed encompassed hereby and fall within the scope of the present inventive discovery. Further in this regard, it is noted that the rights of the present inventors in the instantly disclosed invention are only to be limited by the scope of the claims appended hereto, and the equivalents thereof.

The compounds of Formulas I, II and III, disclosed herein, all possess an ability to release nitric oxide (NO) in vivo, in a stable controlled fashion. This controlled release of NO makes the compounds of Formulas I, II and III valuable as pharmaceutical agents in the treatment of cardiovascular disorders, such as hypertension, arteriosclerosis, cerebral vasospasm and coronary vasospasm; any cardiovascular disorder which is treatable by lowering blood pressure is treatable using the compounds of the present invention.

While all of the compounds of Formulas I, II and III disclosed herein are considered valuable in treating cardiovascular disorders and are effective in the methods of the present invention, some of the compounds encompassed hereby are thought preferred. Such preferred compounds possess an unexpectedly high stability and have a long length of in vivo activity associated therewith. In this regard, compounds of Formulas I, II and III which are prepared by reacting nitric oxide with polyamines containing both primary and secondary amino groups, have been found to possess an unexpected high degree of stability and long lengths of action in vivo. Even so, compounds prepared from polyamines containing only secondary amines, and compounds prepared from polyamines containing only tertiary and secondary amines are still relatively stable and long acting. Methods of preparing the compounds of Formulas I, II and III from polyamines are discussed below.

Regarding the presence of the $N_2O_2^-$ group and the proton charge ($H^+$) in compounds of Formulas I, II and III, the following is noted. When compounds of the present invention are prepared (e.g., by reacting a polyamine with nitric oxide), the $N_2O_2^-$ groups preferably and generally form on secondary amines and less preferably form on primary amines. Moreover, the $N_2O_2^-$ groups under most reaction conditions will not form on a tertiary or highly hindered amine moiety. Regarding the proton shown in Formulas I, II and III, the same is in reality labile and will tend to drift around, so that each formula shown may be a mixture of tautomers.

Therefore, the position of $H^+$ and $N_2O_2^-$ attachment may differ from one complex to another (and even from one molecule to another in a given preparation).

Regarding specific methods of preparing the compounds of Formulas I, II and III encompassed hereby, the following discussions of synthesis procedures are provided, however, they are not meant to limit methods which may be used for preparing the compounds encompassed hereby.

In order to prepare compounds of the present invention, it is thought preferred if appropriate polyamines are obtained first and then reacted with nitric oxide under suitable conditions to give the desired compound. Under such a synthesis procedure, many of the polyamines needed to prepare compounds according to the present invention are commercially available. For example, Aldrich Chemical Co., Milwaukee, Wisc., produces many of the polyamines utilized herein for forming compounds according to the present invention. Exemplary of some polyamines commercially available from Aldrich Chemical Company and which are useful in the present invention are the following:
N,N,N'-trimethyl-1,3-propanediamine,
diethylenetriamine,
N,N'-bis(3-aminopropyl)-1,4-butanediamine,
N,N'-bis(3-aminopropyl)ethylenediamine,
N,N'-bis(3-aminopropyl)-1,3-propanediamine,
1-(2-aminoethyl)piperazine,
N-(2-aminoethyl)-1,3-propanediamine,
3,3'-iminobispropylamine, and
triethylenetetramine.

The above list is not exhaustive of commercially available polyamines which may be reacted with NO to form compounds of the present invention.

Polyamines useful in preparing the compounds of the present invention may also be synthesized utilizing procedures well known by those of ordinary skill in the art. The following are exemplary synthesis procedures which may be utilized, alone or in combination, as desired.

Certain diamines useful in preparing compounds encompassed by the present invention may be prepared according to the procedures set forth by D. O. Alonso Garrido et al, in *J. Org. Chem.*, Vol. 49, p. 2021-2023 (1984), as shown in the following Scheme I :

Scheme I

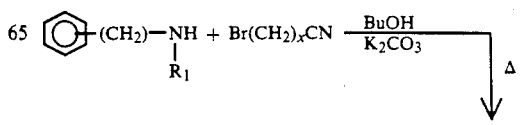

Scheme I
-continued

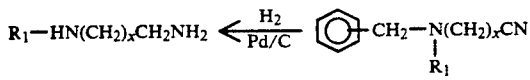

Garrido et al prepare compounds where $R_1$ is $C_{1-4}$ alkyl and x is 3, but note that $R_1$ and x may be varied with no change in the method. The reaction of the secondary amine with an alkyl halide is a well known method of forming a C—N bond, and the substituted benzylamines used in the method are usually commercially available as are the halonitriles.

From the compounds produced in Scheme I, there may be obtained more substituted derivatives using successive protection/deprotection methods which are well known to those skilled in the art. For example, the following methods may be used:

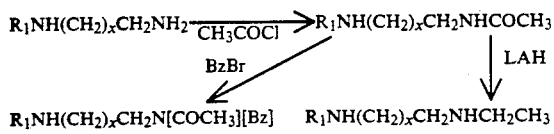

By varying the derivatizing groups and the sequence of the reactions, it is possible to produce any desired substitution pattern. The protecting groups available for use are well known. They include but are not limited to formyl, acetyl, benzyl, benzoyl, trifluoromethyl, t-butoxy-carbonyl, 2,3-dimethoxybenzoyl, phthaloyl and 2,2,2-trichloro-t-butoxycarbonyl. The procedures for the use of and removal of these groups are well known but in any case, specific applications to polyamines are given in the references cited for the production of tri-amines and tetraamines below.

Methods for preparing triamines, which are in turn useful in preparing the compounds of the present invention, are also well known. For example, preparation methods applicable to preparing triamine analogues to the Formula I compounds herein taught are disclosed by R. J. Bergeron, *Accts. Chem. Res.*, Vol. 19, p. 105-113(1986). The chemistry taught by Bergeron is essentially identical to the above discussed diamine case (i.e., alkylation with a halonitrile and subsequent reduction to the amine followed by selective protection and deprotection of the three amine sites). Moreover, Bergeron teaches the preparation of a compound of the formula:

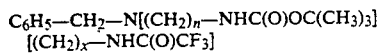

which provides a starting material for many similar N-substituted compounds, since the three protecting groups may be independently removed to unmask a desired amine, which may then be derivatized by known methods (e.g., see R. J. Bergeron et al, *J. Org. Chem.*, Vol. 49, p. 2997-3001(1984)).

Methods similar to those discussed above may also be used to prepare tetraamine analogues to compounds encompassed hereby. For example, R. J. Bergeron et al, *J. Org. Chem.*, Vol. 53, p. 3108-3111(1988) disclose the preparation of the following tetra-protected amine:

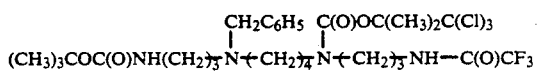

which allows for differentiation of all four nitrogens. As stated by Bergeron et al, the procedure they utilize would work equally well for any other tetraamine, since the numbers of intervening methylene groups (x, y and z in Formula I) do not influence the protection/deprotection steps and can independently be varied by selection of appropriate nitrile and amine starting materials.

Additional preparation techniques for preparing di-, tri- and tetra-amines, which are useful in preparing analogous compounds of the present invention, are disclosed by B. Carboni et al, *Tet. Let.*, Vol. 29, p. 1279-1282(1988). The disclosed techniques are based on coupling dichloroboranes with azides, such as shown in Scheme II :

Scheme II

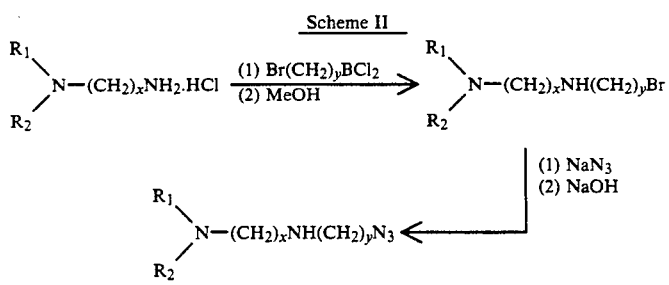

Use of such techniques in combination with protection/deprotection techniques discussed above provides polyamines useful in preparing many of the compounds of Formulas I or II, herein disclosed.

Polyamines useful in preparing compounds of Formula II herein, may be prepared as described above for diamines, except the starting materials utilized are commercially available protected versions of piperidine and piperazine. Standard synthetic methods are then used to substitute the protecting groups with alkyl or alkylamino chains and deprotect the amino groups where necessary.

Additionally, a general method for preparing starting materials for certain aminoalkyl pyridine Formula III compounds has been given by H. E. Reich et al, *J. Amer. Chem. Soc.*, 77, 5434-5436, 1955; G. Magnus et al, *ibid.*, 78, 4127-4130, 1956). The method involves the reaction of commercially available 2,3 or 4-vinylpyridines with a wide range of primary amines. In the preparation of materials with g>2, the pyridyl moiety is sufficiently far removed from the amino moiety that it may be treated as any other group and the usual standard methods as described above for building amines may be employed.

Once a suitable polyamine has been prepared or commercially purchased, it may then be reacted with nitric oxide in the following manners, to give a Formula I, II or III compound of the present invention.

The nitric oxide-polyamine complexes of the present invention are obtainable by reacting suitable polyamines with nitric oxide in a method similar to that taught by R. S. Drago et al, *J. Am. Chem. Soc.*, Vol. 83, p. 1819–1822 (1961). Drago's method, if used to prepare the inventive compounds herein disclosed, would entail bubbling nitric oxide into a cold solution ($\approx -78°$ C.) of the appropriate polyamine and allowing the formed product to precipitate. Alternatively, high pressure techniques are also taught by R. S. Drago in the cited reference for forming nitric acid adducts, and the same are generally applicable herein. During formation of the polyamine-nitric oxide adducts herein taught, it is noted that only one $N_2O_2^-$ group attaches to each molecule regardless of the number of nitrogen atoms present on the chosen polyamine. This is due to the fact that the nitric oxide adduct salt immediately precipitates upon formation, and is thus not available for further reaction with the nitric oxide under either method taught by Drago et al. However, polyamines with sufficient solubility as the mono-$N_2O_2^-$complex would be capable of forming bis-adducts. The cited Drago et al reference is expressly incorporated by reference herein.

Once the desired nitric oxide adduct according to the present invention has been prepared, a pharmaceutically acceptable salt thereof, as defined herein, may be prepared if desired. Exemplary of techniques used to prepare such salts would be the preparation of the potassium salt of one of the Formula I, II or III compounds herein disclosed by reacting the same with potassium hydroxide in an ethanol or similar solution. Similarly, the sodium, calcium and magnesium salts, among others, could be prepared.

Having provided general methods, procedures and discussions relating to the production of Formula I, II and III compounds, the following Experimental Section is provided. The Experimental Section is divided into two parts, the first relating to compound synthesis and the second relating to pharmacological testing.

EXPERIMENTAL SECTION

Compound Synthesis

All melting points are uncorrected. The IR spectra were determined with a Perkin-Elmer Model 467 grating infrared spectrophotometer. The UV spectra were determined with a Spectronic 710. The $^1$H NMR spectra were determined at 200 MHz with a Varian Model XL-200 NMR spectrometer. The $^{13}$C NMR spectra were determined at 50 MHz. The chemical shifts are expressed in $\delta$ values (ppm) relative to either tetramethylsilane or sodium 3-(trimethylsilyl)propionate-d$_4$ as internal standards. Elemental analyses were performed by Galbraith Laboratories, Knoxville, Tenn.

Except as noted here, all reagents and amine samples were obtained from Aldrich Chemical Company (St. Louis, Missouri). Spermine and spermidine were from Sigma Chemical Company. N,N'-Dimethyl-1,4-butanediamine was from Pfaltz and Bauer (Waterbury, Conn.). Nitric oxide was the commercial grade from Matheson Gas Products.

Reactions under pressure were conducted in glass bottles on a standard Model 3911 hydrogenation apparatus (Parr Instrument Company, Moline, Ill.).

EXAMPLE 1

N,N'-Dimethyl-1,4-butanediamine bis (nitric oxide) adduct

A solution of N,N'-dimethyl-1,4-butanediamine (9.50 g, 81.7 mmol) in 100 mL anhydrous ethyl ether was placed in a standard glass hydrogenation bottle. Nitrogen gas was bubbled through this solution for 5 minutes and the bottle was then placed in the Parr apparatus. The solution wa cooled by packing dry ice around the bottle and NO was admitted to a pressure of 70 psig. The unstirred mixture wa kept in the dry ice for 4 hours and then allowed to warm slowly to room temperature and stand under NO for 20 hours. During this time, the pressure fell to 45 psig which was then vented and the reaction flushed with nitrogen. The voluminous white precipitate was filtered, washed with ether and then dried in vacuo 2 hours to afford the product as an amorphous white powder. Yield 3.21 g (22%). m.p. 112°–114° C. dec. IR (KBr pellet, approximate intensities shown as : i=intense, m=medium, w=weak, br=broad) 2600–3050 (i, br), 2400 (i, br), 1590 (w), 1510 (m), 1470 (m), 1380 (i), 1270 (m), 1160 (i, br), 1075 (m), 985 (i), 930 (i), 810 (w), 750 (w), 650 (w): $^1$H NMR (D$_2$O) $\delta$ 1.41 (2H, m), 1.72 (2H, m), 2.67 (3H, s), 2.74 (3H, s), 2.97 (4H, dt); $^{13}$C NMR (D$_2$O) 26.12, 26.53, 35.82, 45.16, 51.94, 56.73 ppm.

EXAMPLE 2

Bis2-(2-methylaminoethyl)pyridine1 bis (nitric oxide) adduct

A solution of 2- (2-methylaminoethyl)pyridine (11.2 g, 82.2 mmol) in 100 mL anhydrous ethyl ether was deoxygenated as above and placed in the Parr apparatus. The solution was cooled in dry ice and NO gas was admitted to a pressure of 75 psig. The unstirred mixture was kept in dry ice for 3 hours and then allowed to warm slowly to room temperature and stand under NO for 20 hours. The pressure had fallen to 40 psig after 3 hours, was adjusted back to 75 psig at room temperature and fell back to 40 psig overnight. The colorless crystalline precipitate was filtered, washed with ether and then dried in vacuo 2 hours to afford the product as beautiful needles. Yield 5.97 g (44%). m.p. 74°–75° C. dec. IR (KBr pellet) 2900–3050 (m, br), 2780 (i, br), 2300–2450 (m, br), 1590 (i), 1565 (m), 1510 (m), 1480 (m), 1440 (i), 1370 (i), 1200 (w), 1160 (i, br), 1120 (w), 1080 (w), 985 (m), 940 (m), 795 (m), 760 (i); $^1$H NMR (D$_2$O) $\delta$ 2.70 (3H, s), 2.72 (3H, s), 2.78 (2H, t), 3.17 (2H, t), 3.32 (2H, t), 3.38 (2H, t), 7.24–7.41 (4H, m), 7.77 (1H, dt), 7.83 (1H, dt), 8.42 (1H, dm), 8.47 (1H, dm).

EXAMPLE 3

Spermine bis(nitric oxide) adduct

A solution of spermine (8.12 g, 40.1 mmol) in 150 mL dry tetrahydrofuran was deoxygenated with nitrogen and placed in the Parr apparatus. The solution was maintained at room temperature (ca. 22° C.) and NO gas was admitted to a pressure of 75 psig. Within 20 minutes, the solution became cloudy at the surface and solid began forming. The pressure was kept at 70–75 psig by occasional addition of NO and the solution shaken intermittently for 3 days. The excess pressure was vented and the mixture flushed with nitrogen for 5 minutes. The voluminous white precipitate was filtered, washed with ether and then dried in vacuo 2 hours to afford the product as a white amorphous powder. Yield 2.96 g (28%). m.p. 105°–107° C. dec. IR (KBr pellet) 2200–3200 (i, br), 1580 (m, br), 1470 (m, br), 1380 (m) 1270 (w), 1150 (i, br), 940 (m, br); $^1$H NMR (D$_2$O) δ 1.38 (2H, m), 1.58 (4H, m), 1.75 (2H, m), 2.70–2.85 (8H, m), 2.96 (4H, dt); $^{13}$C NMR (D$_2$O) 26.35, 27.68, 30.00, 31.59, 40.97, 41.04, 48.56, 50.67, 54.37, 56.44.

EXAMPLE 4

Preparation of N-Propyl-1,3-propanediamine bis(nitric oxide) adduct

A solution of N-propyl-1,3-propanediamine (11.0 g, 94.6 mmol) in 100 mL anhydrous ethyl ether was deoxygenated with nitrogen and placed on the Parr apparatus. The solution was cooled to −20° C. in a dry ice/carbontetrachloride bath and NO gas was admitted to a pressure of 75 psig. After 4 hours, the reaction was allowed to warm to room temperature and the pressure was adjusted up to 75 psig again. After 20 hours, the excess pressure was vented and the mixture flushed with nitrogen for 5 minutes. The white precipitate was filtered, washed with ether and dried in vacuo 2 hours to afford the product as a white amorphous powder. Yield 1.61 g (9.7%). m.p. 97°–99° C. dec. IR (KBr pellet) 2700–3100 (i, br), 2500 (i, br), 2130 (m, br), 1640 (w), 1540 (w), 1470 (w), 1370 (i), 1270 (m), 1225 (i), 1170 (i), 1155 (m), 1090 (w), 970 (m), 930 (i), 780 (w); $^1$H NMR (D$_2$O) δ 0.90 (3H, t), 1.34 (2H, m), 1.69 (2H, m), 2.88 (2H, t), 3.03 (2H, t), 3.06 (2H, t); $^{13}$C NMR (D$_2$O) 13.57, 22.28, 26.91, 40.55, 53.81, 58.93.

EXAMPLE 5

Spermidine bis(nitric oxide) adduct

A solution of spermidine (9.5 g, 65.4 mmol) in 100 mL dry tetrahydrofuran was deoxygenated with nitrogen and placed in the Parr apparatus. The solution was maintained at room temperature (ca. 22° C.) and NO gas was admitted to a pressure of 75 psig. The pressure was kept at 70–75 psig by occasional addition of NO and the solution shaken intermittently for 3 days. The excess pressure was vented and the mixture flushed with nitrogen for 5 minutes. The oily yellow solid was separated by decanting the ether and triturated with absolute ethyl alcohol to produce a white powder which was filtered, washed with ether and dried in vacuo. Yield 0.85 g (6.3%). m.p. 92°–94° C. dec. IR (KBr pellet) 2200–3200 (i, br), 2150 (w, br), 1570 (m, br), 1470 (m), 1350 (m, br), 1270 (m), 1180 (m. br), 930 (m, br); $^1$H NMR (D$_2$O) 1.3–1.5 (2H, m), 1.5–1.7 (4H, m), 2.7–2.9 (4H, m), 2.9–3.0 (4H, m); $^{13}$C NMR (D$_2$O) 26.03, 29.22, 30.00, 40.92, 42.53, 54.34, 56.38.

PHARMACOLOGY

The effects of the polyamine-nitric oxide adducts encompassed hereby on the mean arterial pressure (MAP) of male Sprague-Dawley rats were measured using a pressure transducer connected to the left carotid artery via a catheter containing heparinized saline. The MAP was recorded on a Grass Recorder. The rat was anesthetized with nembutal at an initial dose of 35 mg/kg and recurrent smaller injections as needed. The test substance was dissolved in 0.9% sodium chloride and injected at the doses shown below into the rat via a catheter in the left jugular vein. The effects on the MAP are recorded in Table I.

TABLE I

| | Hypotensive Effects of Polyamine-Nitric Oxide Adducts | | | |
|---|---|---|---|---|
| | | MAP (in mm of Hg) | | |
| Ex. | Dose (μmol/kg) | Initial | Minimum | Final (time post-injection) |
| Ex. 3[1] | 3 μmol of spermine.2NO/kg | 126 | 42 | 74 (at 54 min) |
| Ex. 5 | 6 | 132 | 56 | 96 (at 27 min) |
| Ex. 2 | 7.5 | 128 | 40 | 116 (at 22 min) |
| Ex. 4 | 14 | 84 | 35 | 35 (at 19 min) |
| | 14 | 91 | 31 | 80 (at 69 min) |
| Ex. 1 | 14 | 84 | 39 | 81 (at 36 min) |

[1]Mixed with roughly equimolar spermine free base.

In the tests of Table I, SNP (sodium nitroprusside) was used as a control. It is a known vasodilator. Free spermine was also studied as a control, because it was a known contaminant of the spermine·2NO sample tested above. Neither control had as long a duration of action as the compounds of Table I displayed.

The duration of action of the compounds of this invention is significantly longer than those of the compounds described in Ser. No. 07/316,958, 07/409,552 and 07/423,279, all of which had a duration of action of 15 minutes or less in similar tests. Thus, the present compounds have the advantage of not having to be administered as frequently.

Additionally, a saline solution containing 4 mg/mL of spermine·2NO was prepared and injected at several dose levels into a 480-g male Sprague Dawley rat anesthetized with nembutal and catheterized via the right carotid artery and right femoral vein. Five intravenous injections at successively increasing doses were administered with the results shown in Table II.

TABLE II

| Dose-Response Data for Spermine.2NO (Example 3) | | | | |
|---|---|---|---|---|
| dose (μmol/kg) | blood pressure readings (mm of Hg) | | | time to recover |
| | baseline | minimum | observed-drop | |
| 0.1 | 130/90 | 100/70 | approx. 20* | no recovery in 40 min. |
| 0.3 | 95/65 | 70/48 | approx. 25 | fluctuated- difficult to quantify |
| 1. | 95/65 | 62/45 | approx. 28 | 38 min. to baseline |
| 3. | 97/70 | 55/30 | approx. 40 | not determined |
| 10 | 90/65 | 55/33 | approx. 40 | not quantifiable; rat began waking at 10 min. post-injection |

*Because there was no recovery in 40 minutes, it is questionable whether this result reflects a reliable response.

Based upon results obtained in Tables I and II, it is fully established that the nitric oxide adducts encompassed hereby are useful in treating cardiovascular disorders such as hypertension in mammals, including man.

PHARMACEUTICAL COMPOSITIONS

Due to their chemical structures, the compounds of the present invention are preferably administered intravenously and are made into pharmaceutical compositions by combination with appropriate pharmaceutically acceptable carriers or diluents. For example, Formula I, II and III compounds provided herein may be formulated into injectable preparations in ways usual for such a route of administration, and the following methods and excipients are exemplary of such usual and acceptable means. Even so, the following should not be considered to limit the scope of the present invention with respect to pharmaceutical compositions or routes of administration.

The compounds of the present invention may be formulated into preparations for injection by dissolving, suspending, or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives. Parenteral administration of the compounds of the present invention may also be had by a pharmaceutically acceptable carrier such as dextrose, sterile water for injection, USP, or by normal saline.

The amount of the compounds of the present invention to be used as cardiovascular agents, of course, varies according to the compounds administered, the type of cardiovascular disorder encountered and the route of administration chosen. A suitable dosage is thought to be about 0.01 to 10.0 mg/kg/day, where one is treating hypertension, arteriosclerosis, cerebral vasospasm or coronary vasospasm and the route of administration is intravenous. The preferred dosage is, of course, that amount just sufficient to treat a particular cardiovascular disorder and would preferably be an amount from about 0.05 to 5.0 mg/kg/day.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A compound of Formula II:

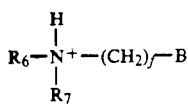

Formula II wherein:

B is 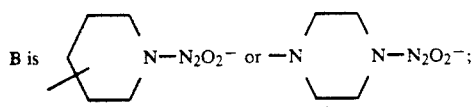

and $R_6$ and $R_7$, same or different, are hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl; f is 0 to 12, with the proviso that when B is the substituted piperazine moiety

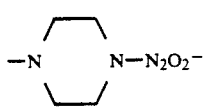

then f is 2 to 12; or
a pharmaceutically acceptable salt thereof.

2. A compound as recited in claim 1, wherein: $R_6$ and $R_7$, same or different, are hydrogen, $C_{5-6}$ cycloalkyl, $C_{1-4}$ straight or branched chain alkyl, benzyl or acetyl.

3. A compound as recited in claim 2, wherein: $R_6$ and $R_7$, same or different, are hydrogen, methyl, ethyl, benzyl or acetyl; and f is 2 to 4.

4. A compound as recited in claim 3, wherein: $R_6$ and $R_7$, same or different, are hydrogen, methyl, or acetyl.

5. A compound of Formula III:

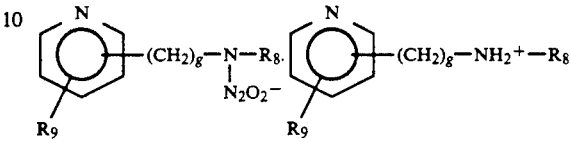

Formula III wherein:

$R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl or 2,2,2-tri-chloro-t-butoxycarbonyl;

$R_9$ is hydrogen or a $C_1-C_{12}$ straight or branched chain alkyl; and g is 2 to 6; or a pharmaceutically acceptable salt thereof.

6. A compound as recited in claim 5, wherein: $R_8$ is $C_{5-6}$ cycloalkyl, $C_{1-4}$ straight or branched chain alkyl, benzyl or acetyl.

7. A compound as recited in claim 6, wherein:

$R_8$ is methyl, ethyl, benzyl or acetyl; and g is 2 to 4.

8. A compound as recited in claim 7, wherein: $R_8$ is methyl or acetyl.

9. A compound as recited in claim 5, wherein the Formula III compound is:

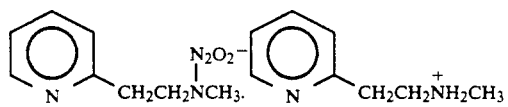

or a pharmaceutically acceptable salt thereof.

10. A method of treating cardiovascular disorders which are treatable by lowering blood pressure, the method comprising:

administering to a mammal, in need thereof, an effective amount of a compound of Formula II:

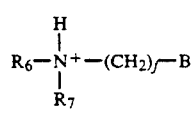

Formula II wherein:

B is 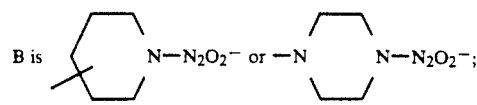

$R_6$ and $R_7$, same or different, are hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl;

f is 0 to 12, with the proviso that when B is the substituted piperazine moiety

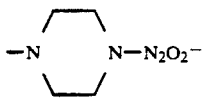

then f is 2 to 12; or
a pharmaceutically acceptable salt thereof.

11. A method of treating cardiovascular disorders which are treatable by lowering blood pressure, the method comprising:
administering to a mammal, in need thereof, an effective amount of a compound of Formula III:

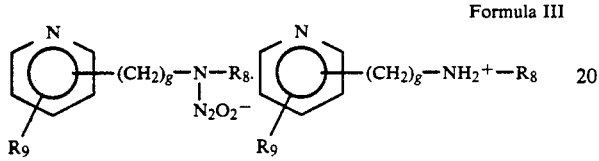

Formula III wherein:
$R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl;
$R_9$ is hydrogen or a $C_1$-$C_{12}$ straight or branched chain alkyl; and
g is 2 to 6; or
a pharmaceutically acceptable salt thereof.

12. A pharmaceutical composition, comprising:
an effective amount of a compound of Formula II for treating a cardiovascular disorder which is treatable by lowering blood pressure;

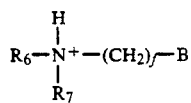

Formula II wherein:

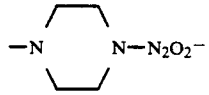

$R_6$ and $R_7$, same or different, are hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl,
f is 0 to 12, with the proviso that when B is the substituted piperazine moiety then f is 2 to 12, or
a pharmaceutically acceptable salt thereof; and
a pharmaceutically acceptable carrier therefor.

13. A pharmaceutical composition, comprising:
an effective amount of a compound of Formula III for treating a cardiovascular disorder that is treatable by lowering blood pressure:

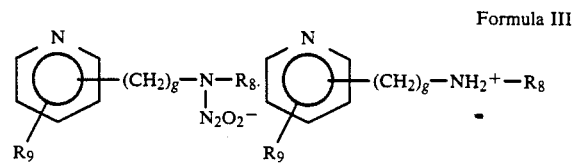

Formula III wherein:
$R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl,
$R_9$ is hydrogen or a Chd $1$-$C_{12}$ straight or branched chain alkyl, and
g is 2 to 6, or
a pharmaceutically acceptable salt thereof;
and a pharmaceutically carrier therefor.

* * * * *